(12) United States Patent
Rakshit et al.

(10) Patent No.: US 11,372,392 B2
(45) Date of Patent: Jun. 28, 2022

(54) SYSTEM AND METHOD OF PRINTING 3D BIOSTRUCTURES

(71) Applicant: INTERNATIONAL BUSINESS MACHINES CORPORATION, Armonk, NY (US)

(72) Inventors: Sarbajit K. Rakshit, Kolkata (IN); Mukundan Sundararajan, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 84 days.

(21) Appl. No.: 17/025,279

(22) Filed: Sep. 18, 2020

(65) Prior Publication Data

US 2022/0091579 A1    Mar. 24, 2022

(51) Int. Cl.
G05B 19/40 (2006.01)
A61F 2/00 (2006.01)
(Continued)

(52) U.S. Cl.
CPC ........ G05B 19/4099 (2013.01); A61F 2/0063 (2013.01); B33Y 10/00 (2014.12);
(Continued)

(58) Field of Classification Search
CPC ...... G05B 19/4099; G05B 2219/49023; A61F 2/0063; A61B 2017/00526; B33Y 10/00
See application file for complete search history.

(56) References Cited

U.S. PATENT DOCUMENTS

| 8,516,691 B2 * | 8/2013 | Gilad | A61B 1/041 29/830 |
| 10,251,580 B2 * | 4/2019 | Carron | A61B 5/073 |

(Continued)

FOREIGN PATENT DOCUMENTS

| CN | 104337589 A | 2/2015 |
| CN | 104768586 A | 7/2015 |

(Continued)

OTHER PUBLICATIONS

Murphy et al.; 3D Bioprinting of Tissues and Organs; Aug. 2014; Nature Biotechnology; pp. 1-13 (Year: 2014).*

(Continued)

Primary Examiner — Bayan Salone
(74) Attorney, Agent, or Firm — Haley J. McClory

(57) ABSTRACT

A computer-implemented method of internally printing a biostructure on a damaged area of a patient. The method includes: assembling a first bioprinter capsule and a first cartridge capsule to form an assembled bioprinter internally within the patient based, at least in part, on directing one or more magnetic fields towards a first bioprinter capsule and a first cartridge capsule, moving the assembled bioprinter to the internally damaged area of the patient based, at least in part, on altering the one or more external magnetic fields directed towards the assembled bioprinter, and printing, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

20 Claims, 7 Drawing Sheets

(51) Int. Cl.
*B33Y 10/00* (2015.01)
*G05B 19/4099* (2006.01)
*A61B 17/00* (2006.01)

(52) U.S. Cl.
CPC ........... *A61B 2017/00039* (2013.01); *A61B 2017/00526* (2013.01); *G05B 2219/49023* (2013.01)

(56) References Cited

U.S. PATENT DOCUMENTS

| | | | | |
|---|---|---|---|---|
| 11,167,375 | B2* | 11/2021 | Schiffres | B33Y 80/00 |
| 2015/0246072 | A1* | 9/2015 | Bhatia | A61L 27/38 |
| | | | | 424/93.7 |
| 2016/0288414 | A1* | 10/2016 | Ozbolat | A61F 2/2875 |
| 2018/0339455 | A1* | 11/2018 | Cohen | B29C 64/25 |
| 2019/0367884 | A1* | 12/2019 | Satchi-Fainaro | C12N 5/069 |
| 2020/0047288 | A1* | 2/2020 | Schiffres | B32B 15/01 |
| 2020/0049415 | A1* | 2/2020 | Schiffres | B33Y 10/00 |
| 2021/0007778 | A1* | 1/2021 | Shoham | A61B 34/77 |
| 2021/0145872 | A1 | 5/2021 | Hariri | |

FOREIGN PATENT DOCUMENTS

| | | | | |
|---|---|---|---|---|
| WO | 2015066705 | A1 | 5/2015 | |
| WO | WO-2015066705 | A1 * | 5/2015 | ......... B29C 67/0055 |
| WO | 2017004623 | A1 | 1/2017 | |
| WO | 2017184839 | A1 | 10/2017 | |
| WO | WO-2017184839 | A1 * | 10/2017 | ............ A61L 27/36 |

OTHER PUBLICATIONS

Yang et al.; Noncontact Orientation of Objects in Three-Dimensional Space using Magnetic Levitation; Sep. 9, 2014; pp. 1-6 (Year: 2014).*
Chowdry; Liver Success Holds Promise of 3D Organ Printing; Mar. 5, 2018; pp. 1-3 (Year: 2018).*
Lenrosen; 3D Printing Body Parts is No Longer Science Fiction; Jul. 8, 2018; pp. 1-2 (Year: 2018).*
"3D Bioprinting | 3D Bio-Printer | Printing Body Parts", RF Wireless World, <https://www.rfwireless-world.com/Tutorials/3D-Bioprinting-and-3D-Bio-Printers-in-medical.html>, printed Jan. 29, 2020, 4 pages.
"3D Bioprinting of Living Tissues", Wyss Institute, <https://wyss.harvard.edu/technology/3d-bioprinting/>. printed Jan. 29, 2020, 6 pages.
"3D Printing Body Parts is No Longer Science Fiction", Cellink, <https://cellink.com/3d-printing-body-parts-no-longer-science-fiction/, Jul. 9, 2018, pp. 1-7.
"Printing the future: 3D bioprinters and their uses", Australian Academy of Science, <https://www.science.org.au/curious/people-medicine/bioprinting>.last updated Feb. 29, 2016, pp. 1-10.
Chowdhury, "Liver success holds promise of 3D organ printing", <https://www.ft.com/content/67e3ab88-f56f-11e7-a4c9-bbdefa4f210b>. Financial Times, Mar. 5, 2018, pp. 1-5.
Murphy, J., "7 amazing body parts that can now be 3D printed", MDLinx, , <https://www.mdlinx.com/internal-medicine/article/2668>.,Sep. 19, 2018, 8 pages.
Murphy, S. et al., "3D Bioprinting of Tissues and Organs", Nature Biotechnology, Aug. 2014, vol. 32 No. 8, <https://www.researchgate.net/publication/264500820_3D_Bioprinting_of_Tissues_and_Organs>. 14 pages.
Subramaniam et al., "Noncontact orientation of objects in three-dimensional space using magnetic levitation", www.pnas.org/cgi/doi/10.1073/pnas.1408705111 Downloaded, Sep. 9, 2014, vol. 111, No. 36, pp. 12980-12985.

* cited by examiner

SYSTEM AND METHOD OF PRINTING 3D BIOSTRUCTURES

BACKGROUND

The present invention relates generally to the field of 3D printing, and more particularly to the use of 3D printer technology to print biological tissue structures, or bio structures.

3D printing, also known as additive manufacturing, allows for the building of complex and detailed structures by laying one layer of a structure upon another that, once compiled, produces a 3D structure. The 3D printing process generally begins with a generated file of the desired 3-Dimensional structure. The file is then sliced into X, Y, and Z-axis coordinates that act as directions to the 3D printer on how to build the 3D structure. The level of detail desired of the finished structure is often controlled by the thickness of each layer. This layer thickness is controlled by the user but is often limited by the sensitivity and capabilities of the 3D printer machine itself. While traditional methods of 3D printing include using polymers, such as polylactic acid (PLA), advancements in 3D printing technology have resulted in new and innovative approaches for printing biological structures using biological materials.

3D printing of biological structures with biological materials and/or biocompatible materials has revolutionized how scientists and medical professionals approach patient treatment. Now, scientists are able to use materials compatible with living organisms to build not only layers of cells, but functional and complete structures, such as a human ear and vascular grafts. These structures can be built using materials traditionally found in organisms, such as gelatin or collagen, but synthetic molecules specifically engineered to mimic biostructures may also be utilized. Recent innovations have further expanded this list of available biological printing materials to include individual cells and allow for the 3D printing of tissue.

SUMMARY

According to one embodiment of the present invention, a computer-implemented method for 3D printing a biostructure on an internally damaged area of a patient is disclosed. The computer-implemented method includes assembling a first bioprinter capsule and a first cartridge capsule to form an assembled bioprinter internally within the patient based, at least in part, on directing one or more external magnetic fields towards a first bioprinter capsule and a first cartridge capsule. The first bioprinter capsule includes a first magnetic signature and at least one interlocking surface. The first cartridge capsule includes a second magnetic signature and at least one interlocking surface. The computer-implemented method further includes moving the assembled bioprinter to the internally damaged area of the patient based, at least in part, on altering the one or more external magnetic fields directed towards the assembled bioprinter. The computer-implemented method further includes printing, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

According to another embodiment of the present invention, a computer program product for 3D printing a biostructure on an internally damaged area of a patient is disclosed. The computer program product includes one or more computer readable storage media and program instructions stored on the one or more computer readable storage media, the program instructions including instructions to assemble a first bioprinter capsule and a first cartridge capsule to form an assembled bioprinter internally within the patient based, at least in part, on directing one or more external magnetic fields towards a first bioprinter capsule and a first cartridge capsule. The first bioprinter capsule includes a first magnetic signature and at least one interlocking surface. The first cartridge capsule includes a second magnetic signature and at least one interlocking surface. The program instructions further include instructions to move the assembled bioprinter to the internally damaged area of the patient based, at least in part, on altering the one or more external magnetic fields directed towards the assembled bioprinter. The program instructions further include instructions to print, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

According to another embodiment of the present invention, a computer system for 3D printing a biostructure on an internally damaged area of a patient is disclosed. The computer system includes one or more computer system includes one or more computer processors, one or more computer readable storage media, and program instructions stored on the computer readable storage media for execution by at least one of the one or more computer processors, the program instructions including instructions to assemble a first bioprinter capsule and a first cartridge capsule to form an assembled bioprinter internally within the patient based, at least in part, on directing one or more external magnetic fields towards a first bioprinter capsule and a first cartridge capsule. The first bioprinter capsule includes a first magnetic signature and at least one interlocking surface. The first cartridge capsule includes a second magnetic signature and at least one interlocking surface. The program instructions further include instructions to move the assembled bioprinter to the internally damaged area of the patient based, at least in part, on altering the one or more external magnetic fields directed towards the assembled bioprinter. The program instructions further include instructions to print, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

DETAILED DESCRIPTION

Figure 1:
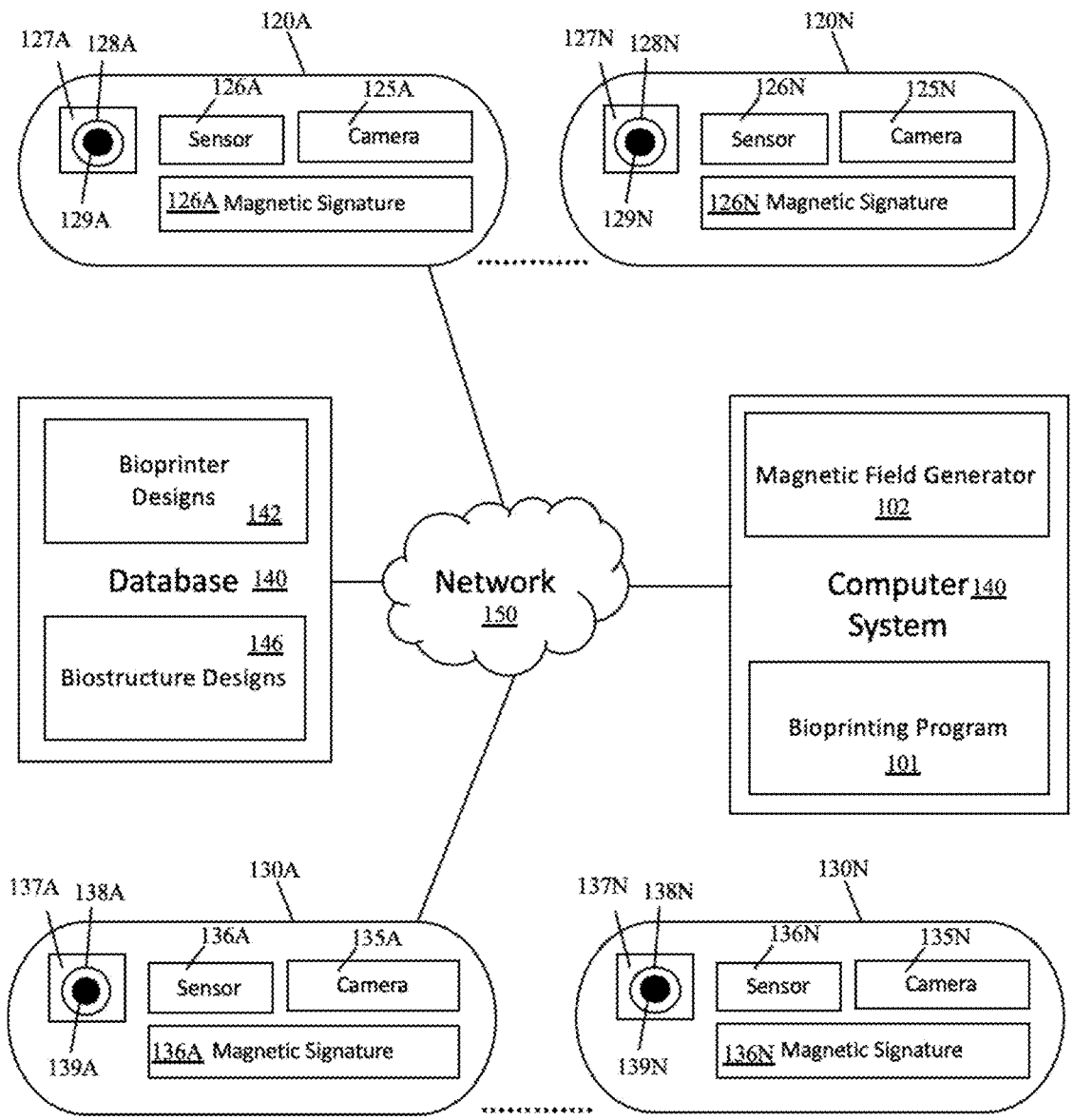
FIG. 1 is a functional block diagram illustrating a computing environment, generally designated 100, suitable for operation of a bioprinting program 101 in accordance with at least one embodiment of the present invention.

As 3D printing technology and innovation have increased, so has the ability to use 3D printing's basic but effective technological principles across numerous scientific and engineering disciplines. One such discipline includes the area of bioprinting. Instead of traditional inks or filaments associated with 3D printing, bioprinters use a combination of biomaterials and growth factors to create tissue-like structures in a layer-by-layer manner. Examples of biomaterials may include, but are not limited to, cells produced from adult stem cells or donor cells, a variety of biomolecules, as well as other biocompatible polymers and synthetic compounds designed to biomimic various tissue or cells commonly found in humans or animals. As a result, bioprinters are able to print complex biostructures designed to function like living tissue. These printed biostructures can be used to perform more accurate pharmaceutical drug trials or could be used as replacement parts where the printed biostructure is grafted onto a living organism. Currently, bioprinter technology allows for the printing of skin, bone, corneas, and other complex vascularized tissues.

Generally, like all 3D printers, bioprinters receive specific instructions for printing a 3D biostructure. These instructions provide complex information for building each layer of the 3D biostructure. This information includes not only the length and width of the area to be printed, but also the height of each layer, if there is more than one type of biomaterial needed to complete each layer, the particular location(s) of each layer where each biomaterial should be printed, and a plurality of other parameters that might be necessary to build more complex biostructures. Traditionally, bioprinters initially print a plurality of layers from a first substance, such as a type of hydrogel, that acts as a base for the biomaterial to attach to. Hydrogel or similar materials may be used to support the biostructure throughout the different layers of the printing process and can be removed or dissolved after bioprinting is completed. After the base is established, the bioprinter begins to print the actual biostructure in a layer-by-layer manner. Each layer may include more than one type of biomaterial. For example, when bioprinting a capillary vessel, one layer may include endothelial cells, pericytes or an external supporting cell type, and hydrogel to support the endothelial cells open to the lumen of the capillary and the outer wall formed from pericytes. The hydrogel or similar materials can be thought of as a type of mold, allowing the cells to be held in place. Once the necessary number of layers have been printed to form the capillary vessel, the cells grow and mature into tissue in the hydrogel mold. Once mature, the supporting hydrogel mold can be removed and the resulting functional vessel can be used for a variety of medical purposes.

Embodiments of the present invention recognize several deficiencies with bioprinting. Current bioprinting technologies require 3D biostructures to be printed in a lab setting and require a significant amount of time for cell structures to grow and mature before the 3D biostructure can be implanted inside a patient. However, patients may be in dire need of such implants and may be required to wait in pain or endure worsening conditions while a biostructure implant is produced and grown in a lab. Alternatively, due to the configuration and size of current bioprinter technology, some areas of the human body where bioprinting could produce immediate relief are only accessible via surgical means. Embodiments of the present invention recognize that one area of the human body where bioprinting would be advantageous is in the digestive tract. Due to the digestive and sometimes corrosive environment of the digestive system, patients often have a difficult time healing damaged areas. Specifically, patients who suffer from diabetes have been shown not only to have a higher incidence of gastric ulcers, but also a more difficult time healing such ulcers. For persistent and severe ulcers, surgery may be the only option. However, invasive surgery can present a variety of potentially negative side effects in of itself.

Embodiments of the present invention provide one or more of features, characteristics, operations, and/or advantages to the above mentioned deficiencies with bioprinting and generally encompass: (i) an improvement to at least the field of bioprinting and (ii) a technical solution to one or more challenges in the field of bioprinting. More particularly, embodiments of the present invention improve the performance of healing internally damaged areas of the human body, including the digestive tract, using methods associated with bioprinting that offer a comprehensive and nonsurgical means for treating patients. The present invention generally includes at least one bioprinter capsule and at least one cartridge capsule, each of which are sized to be swallowed, and a computer system having a program configured to connect the bioprinter capsule and cartridge capsule to form a functional bioprinter assembly, direct the bioprinter assembly to a damaged area within the digestive tract, and manipulate the position of the bioprinter assembly with respect to the damaged area to ultimately graft a 3D printed biological structure onto the damaged area within the digestive tract. In various embodiments of the invention, the bioprinter capsule and cartridge capsule are magnetically coupled in a predetermined arrangement to form an assembled bioprinter by altering one or more external magnetic fields. Similarly, the assembled bioprinter is directed from its assembly location to an area of damaged tissue within the digestive tract by altering one or more external magnetic fields.

Once positioned at the area of damaged tissue, the strength and/or direction of the magnetic fields are programmatically altered to direct the movement of the assembled bioprinter during printing to mimic the movements of a traditional 3D bioprinter. In some embodiments, the bioprinter generates a biostructure that includes two or more distinct biomaterials. In an embodiment, two or more biomaterials are mixed within a single cartridge capsule. In an embodiment, each different biomaterial is located within its own respective capsule. In some embodiments, only one biomaterial cartridge can be magnetically coupled to a bioprinter capsule. Accordingly, when a cartridge capsule requires replacement or a different type of biomaterial is required, a connected cartridge capsule is disengaged, and a subsequently ingested cartridge capsule is magnetically coupled to the bioprinter capsule. In other embodiments, more than one biomaterial capsule can be magnetically coupled to a bioprinter capsule at the same time.

In various embodiments of the present invention, once a printed biostructure is successfully printed onto the damaged area and/or disassembly of the bioprinter assembly is required, one or more external magnetic fields are reconfigured to cause the bioprinter capsule(s) and cartridge capsule(s) to magnetically decouple. The disassembled units, (e.g., the bioprinter capsule and cartridge capsule), may then be allowed to naturally travel through the digestive tract, aided by gravity. In an embodiment, the magnetically decoupled capsules are magnetically guided through the digestive tract via programmatically controlling one or more external magnetic fields.

Accordingly, embodiments of the present invention provide a novel system and method of healing damaged areas internally within the human body, and more particularly, within the digestive tract. The following described embodiments further provide a non-surgical treatment for patient's having damaged digestive tracts that will reduce pain, aid in healing, and eliminate the need for costly pharmaceuticals and/or surgeries, while ensuring the patient's health is not further negatively affected.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention will now be described in detail with reference to the figures. FIG. 1 is a functional block diagram of a computing environment, generally designated 100, for bioprinting biostructures internally in the gastrointestinal tract in accordance with at least one embodiment of the present invention. FIG. 1 provides an illustration of only one implementation and does not imply any limitations with regard to the environments in which different embodiment may be implemented. Many modifications may be made to the depicted environment by those skilled in the art without departing from the scope of the invention as recited by the claims. Moreover, it should be appreciated that embodiments of the present invention are not limited to the gastrointestinal tract and can be practiced in any internal locations of the human body where bioprinting biostructures may be required.

Computing environment 100 includes computer system 110, bioprinter capsules 120A-120N, cartridge capsules 130A-130N, and database 140 interconnected over network 150. Network 150 can be, for example, a telecommunications network, a local area network (LAN), a wide area network (WAN), such as the Internet, or a combination of the three, and can include wired, wireless, or fiber optic connections. Network may include one or more wired and/or wireless networks that are capable of receiving and transmitting data, voice, and/or video signals, including multimedia signals that include voice, data, and video information. In general, network may be any combination of connections and protocols that will support communications between computer system 110, including bioprinting program 101 and magnetic field generator 102, bioprinter capsules 120A-120N, cartridge capsules 130A-130N, database 140, and other computing devices (not shown) within computing environment 100.

In various embodiments of the present invention, computer system 110 can be a laptop computer, tablet computer, netbook computer, personal computer (PC), a desktop computer, a personal digital assistant (PDA), a smart phone, or any programmable electronic device capable of receiving, sending, and processing data. In some embodiments, computer system can be a standalone device, a management server, a web server, a mobile device, or any other electronic device or computing system capable of receiving, sending, and processing data. In other embodiments, computer system 110 can represent a server computing system utilizing multiple computers as a server system, such as in a cloud computing environment. In an embodiment, computer system 110 can represent a computing system utilizing clustered computers and components (e.g. database server computers, application server computers, etc.) that act as a single pool of seamless resources when accessed within computing environment 100. In general, computer system 110 can represent any programmable electronic device or combination of programmable electronic devices capable of executing machine readable program instructions and communicating with bioprinting program 101, magnetic field generator 102, bioprinter capsules 120A-120N, cartridge capsules 130A-130N, database 140, and other devices (not depicted) via a network, such as network 150. Computer system 110, magnetic field generator 102, bioprinter capsules 120A-120N, cartridge capsules 130A-130N, and database 140 may include internal and external hardware components, as depicted and described in further detail with respect to FIG. 7.

Computer system 110 includes bioprinting program 101 and magnetic field generator 102. Although magnetic field generator 102 is depicted in FIG. 1 as being integrated with computer system 110, in alternative embodiments, magnetic field generator 102 is remotely located with respect to computer system 110. As used herein, magnetic field generator 102 shall generally be understood as any device or interconnected devices that are capable of generating a magnetic field(s) to levitate, suspend and/or move an object (e.g., bioprinter capsule, cartridge capsule, or assembled bioprinter located internally within the human body). Magnetic field generator 102 may include any arrangement of magnetic materials, including, but not limited to, one or more of the following: permanent magnets, temporary magnets, such as magnets formed from paramagnetic or diamagnetic materials, and electromagnets that can be programmatically configured and/or controlled by bioprinting program 101. In an embodiment, bioprinting program 101 provides instructions to magnetic field generator 102 that cause the physical arrangement of magnets to be altered. For example, instructions for moving the location of one or more magnets to direct an object, such as a bioprinter capsule, to a damaged area within the gastrointestinal tract. In another example, instructions for moving the location of one or more permanent magnets towards or away from a cartridge capsule, thereby altering a magnetic field strength acting on an object, such as a cartridge capsule. In a further example, instructions for physically moving or angling magnetic material, thereby altering how a magnetic field interacts with an object, such as. In yet another example, physically introducing new magnetic material to magnetic field generator 102 to alter a magnetic field acting on an object, such a bioprinter cartridge capsule.

In some embodiments, magnetic field generator 102 is predominantly comprised of electromagnets. Electromagnets produce a magnetic field only when an electric current is applied to the electromagnetic circuit. In an embodiment, bioprinting program 101 provides instructions to magnetic field generator 102 that cause an electric current applied to an electromagnetic circuit to be altered. In other words, bioprinting program 101 can control the electric current applied to electromagnetic circuits. For example, bioprinting program 101 can provide instructions including, but not limited to: (i) turn on and off an electric current applied to electromagnetic circuits at specific times; (ii) increase or decrease an applied current to an electromagnetic circuit to respectively increase or decrease a magnetic field strength; (iii) fluctuate (i.e., increase and decrease) the magnetic field strength of respective electromagnets at specific times during bioprinter assembly and/or the bioprinting process; (iv) reverse the polarity of an electromagnet; and/or (v) alter the polarity of an electromagnet at specific times during bioprinter assembly and/or the bioprinting process.

In an embodiment, magnetic field generator 102 is a standalone, tube-like device (e.g., similar to a magnetic resonance imaging MRI device) that surrounds a patient's body. In an embodiment, magnetic field generator 102 is a wearable device, such as a belt or band having a plurality of magnets and/or electromagnetics built into the wearable device. In an embodiment, magnetic field generator 102 is at least partially, a handheld wand or probe (e.g., similar in structure to a transducer probe of an ultrasound machine) that includes one or more magnets and/or electromagnets that can be directed towards a particular location of a patient's body. Additionally, while some embodiments of magnetic field generator 102 extend at least the length of the patient's body, other embodiments may extend less than the patient's body (e.g., limited to the patient's area of damage).

In various embodiments of the present invention, each of bioprinter capsules 120A-120N (hereinafter referred to generally as bioprinter capsule 120 unless clarifying remarks are made when referring to more than one bioprinter capsule) include at least one magnetic signature 124A-124N, at least one capsule camera 125A-125N, at least one capsule sensor 126A-126N, and at least one interlocking surface 127A-127N (hereinafter referred to generally as magnetic signature 124, capsule camera 125, capsule sensor 126, and interlocking surface 127, respectively, unless clarifying remarks are made when referring to more than one bioprinter capsule 120). However, it should be appreciated that bioprinter capsules 120A-120N can include additional components or fewer components than those listed above depending on the particular requirements of the bioprinter design. For example, in some embodiments, bioprinter capsule 120 need not include camera 125 and/or sensor 126.

In some embodiments, a single bioprinter capsule includes all of the functional units that form a traditional bioprinter. In other embodiments, a plurality of bioprinter capsules, each having separate, distinct functional units (e.g., power generator or battery, bioprinter hardware and/or software components, and scrubbers/finishers) are assembled to form a fully functional assembled bioprinter. For example, in an embodiment, a functional bioprinter is assembled using three bioprinter capsules—bioprinter capsule 120A, bioprinter capsule 120B, and bioprinter capsule 120C. In this exemplary embodiment, bioprinter capsule 120A includes a battery, bioprinter capsule 120B includes a first portion of bioprinter components, such as printhead or extruder, and bioprinter capsule 120C includes a second portion of bioprinter components, such as a scrubber/finisher (i.e., a device to smooth roughened or irregular edges or surfaces). While the aforementioned example includes three bioprinter capsules, 120A, 120B, and 120C, the functional units and/or functional unit subcomponents that form a bioprinter of the present invention can be encapsulated in a single bioprinter capsule, two or more bioprinter capsules, or any combination thereof depending on the particular application at hand.

For clarity and demonstration, while various embodiments disclosed throughout may generally refer to the bioprinter functional units being encapsulated in a single bioprinter capsule 120, as previously discussed above, any number of bioprinter capsules 120A-120N may be used to form a functional bioprinter assembly. Factors that can affect the number of bioprinter capsules 120A-120N used include, but are not limited to, a patient's ability to swallow a particular sized capsule, the complexity of the 3D biostructure to be printed, and the 3D biostructure itself. For example, if a damaged digestive tract area requires complex bioprinting techniques, different internal bioprinting components may be required to properly print different biostructures, and as a result, may be housed within additional bioprinter capsules 120A-120N.

In various embodiments of the present invention, magnetic signature 124 indicates how the bioprinter capsule 120 will behave when introduced to a magnetic field. In some embodiments, magnetic signature 124 is a predesigned component that enables bioprinting program 101 to control and/or orient bioprinter capsule 120 based, at least in part, on altering at least one of a direction and/or strength of one or more external magnetic fields. Magnetic signature 124 may be incorporated into bioprinter capsule 120 based, at least in part, on one or more of: (i) a single magnetic component positioned either homogenously throughout bioprinter 120 or concentrated at a single location on bioprinter capsule 120; (ii) a distribution of a plurality of magnetic components at predetermined locations internal and/or external to bioprinter capsule 120, (iii) a shape of bioprinter capsule 120 itself, and (iv) a density distribution of bioprinter capsule 120.

In various embodiments of the present invention, magnetic components that form magnetic signature 124 can include, but are not limited to permanent magnets, paramagnetic materials, diamagnetic materials, and electromagnets. Moreover, in addition to controlling the electric current applied to electromagnets of magnetic field generator 102, bioprinting program 101 can likewise provide instructions for controlling the electric current applied to electromagnets that form the magnetic signature of bioprinter capsule 120.

In those embodiments having more than one bioprinter capsule 120, each respective bioprinter capsule 120A-120N used to form a functional assembled bioprinter may have the same or different magnetic signatures 124A-124N. In an embodiment, each bioprinter capsule 120A-120N used to form a functional assembled bioprinter has the same magnetic signature 134A-134N. Accordingly, each bioprinter capsule 120A-120N would react (e.g., orient itself and/or move) in the same way when introduced to a particular magnetic field(s). In an embodiment, each bioprinter capsule 120A-120N used to form an assembled bioprinter has different magnetic signatures 134A-134N, respectively. Accordingly, each bioprinter printer capsule 120A-120N would react (e.g., orient itself and/or move) in a different way when introduced to a particular magnetic field(s). In an embodiment, each bioprinter capsule 120A-120N has multiple magnetic signatures. In an exemplary embodiment, a first bioprinter capsule 120A and a second bioprinter capsule 120B are used to form an assembled bioprinter. In this exemplary embodiment, each of bioprinter capsules 120A and 120B have at least two components that form each capsule's magnetic signature 134A and 134 B, respectively. For example, bioprinter capsules 120A and 120B can have the same permanent magnet component, but bioprinter capsule 120A has a lower density and/or mass than bioprinter capsule 120B. Thus, when bioprinter capsules 120A and 120B are introduced to the same magnetic field(s), such as that provided by magnetic field generator 102, both bioprinter capsules 120A and 120B will be levitated or suspended at particular, distinct positions. However, due to the additional density or mass of bioprinter capsule 120B when compared to the lighter density or mass of bioprinter capsule 120A, bioprinter capsule 120B will be oriented lower than bioprinter capsule 120A. In other embodiments each bioprinter capsule 120 has a different and unique magnetic signature 134 that enables for each bioprinter capsule 120A-120N to be individually manipulated and controlled by bioprinting program 101.

In various embodiments of the present invention, bioprinter capsule 120 may include one or more capsule cameras 125 oriented at different positions around bioprinter capsule 120 to provide different viewing angles of the digestive tract and bioprinting process. Capsule camera 125 captures image data, such as live video, photographs, or diagnostic image data of the digestive tract and/or the bioprinting process. In those embodiments where a bioprinter assembly is formed from more than one bioprinter capsule 120A-120N, capsule camera 125-125N may be located on any number of bioprinter capsules 120A-120N, respectively.

In various embodiments of the present invention, each of bioprinter capsules 120A-120N may further include any number of capsule sensors. Capsule sensors 126A-126N may be one type of sensor or may be any combination of sensors of a type known to one skilled in the art. For example, types of sensors can include, but are not limited to, biosensors able to sense an area of damage through the use of biomarkers, position sensors able to determine the position of bioprinter capsule 120 or the position of bioprinter capsule relative to the position of other additional bioprinter capsules 120A-120N, and magnetic sensors able to determine the position of bioprinter capsules 120A-120N based on interactions within the magnetic field (e.g., Hall Sensors). In embodiments having more than one bioprinter capsule 120A-120N, each of capsule sensors 126A-126N may include the same sensor type, different sensor types, or any possible combination thereof. Capsule sensors 126A-N are capable of transmitting sensor data to bioprinting program 101 via a network, such as network 150.

Bioprinter capsules 120A-120N include interlocking surfaces 127A-127N, respectively. Interlocking surfaces 127A-127N are configured to attach to, connect, or interlock with any number of other additional bioprinter capsules 120A-120N and/or any number of cartridge capsules 130A-130N. Each of bioprinter capsules 120A-120N may include any number of interlocking surfaces that may be located on any portion(s) of a bioprinter capsule. Attaching bioprinter capsules with one another, bioprinter capsules with cartridge capsules, and bioprinter capsules with one another allows for bioprinter capsules 120A-120N housing different bioprinter functional units and cartridge capsules housing different biomaterials to form a unified, functional assembled bioprinter.

In some embodiments, interlocking surface 127 can be specifically shaped in such a way as to enable docking between bioprinter capsules 120A-120N and/or cartridge capsules 130A-130N during bioprinter assembly. For example, interlocking surfaces 127A-127N may be include any number of configurations for connecting a bioprinter capsule with another bioprinter capsule and/or cartridge capsule including, but not limited to: (i) a concaved surfaces to prevent shifting between two interconnected bioprinter capsules and aid in the connection of two, individual bioprinter capsules; (ii) male/female physical connections; (iii) electromagnetic circuits; and (iv) attractive and repellent magnetic field forces.

In some embodiments, interlocking surfaces 127A-127N may further include coupling components 128A-128N, respectively, and/or at least one channel 129A-129N, respectively. Coupling component 128A-128N and channel 129A-129N are hereinafter referred to generally as coupling component 128 and channel 129, respectively, unless clarifying remarks are made when referring to more than one bioprinter capsule.

In some embodiments, coupling component 128 is oriented within the interlocking surface and allows for each bioprinter capsule 120A-120N and/or each cartridge capsule 130A-130N to connect and/or lock to each other. In various embodiments, coupling component 128 can be further configured in any number of ways to enable bioprinter capsules 120A-120N and/or cartridge capsules 130A-130N to connect. Such configurations of coupling component 128 may include, but are not limited to, magnetic material components, electromagnetic circuits, and/or locking circuitry. In an exemplary embodiment having two bioprinter capsules 120A and 120B that need to be connected or interlocked, respective interlocking surfaces 127A and 127B are shaped in such a way to induce alignment of coupling component 128A and coupling component 128B. Once coupling components 128A and 128B are aligned, bioprinting program 101 can cause locking circuits on each coupling component to lock bioprinter capsule 120A to capsule 120B.

In another exemplary embodiment, bioprinter capsule 120A has two interlocking surfaces —$127A_1$ and $127A_2$, and bioprinter capsule 120B has two interlocking surfaces —$127B_1$ and $127B_2$. Each of interlocking surfaces $127A_1$, $127A_2$, $127B_1$ and $127B_2$ includes coupling components $128A_1$, $128A_2$, $128B_1$, and $128B_2$ respectively. Continuing with this exemplary embodiment, bioprinter capsules 120A and 120B and their respective components are configured to align in a parallel manner with interlocking surfaces oriented on the sides, and not the ends, of the capsule. While interlocking surface $127A_1$ may be shaped to induce alignment with interlocking surface $127B_1$, and interlocking surface $127A_2$ shaped to induce alignment with interlocking surface $127B_2$, to prevent misalignment (e.g., interlocking surface $127A_1$ aligns with interlocking surface $127B_2$ and interlocking surface $127A_2$ aligns with interlocking surface $127B_1$) coupling components $128A_1$, $128A_2$, $128B_1$, and $128B_2$ may be configured to produce positive or negative magnetic fields that will oppose misalignment and attract the correct coupling component alignment. Coupling components $128A_1$, $128A_2$, $128B_1$, and $128B_2$ connect and/or lock when properly aligned. Bioprinter capsules 120A-120N may have the same coupling components 128A-128N, different coupling components, or any conceivable combination thereof.

In some embodiments, coupling component 128 is configured to share power and/or transfers electrical signals from one bioprinter capsule to another. For example, coupling component 128 allows for the transfer of power between connected bioprinter capsules. In another example, coupling component 128 allows for the transfer of computer readable program instructions between connected bioprinter capsules. In yet a further example, coupling component allows for the transfer of electric signals, including data, between connected bioprinter capsules. It should be appreciated that bioprinter capsules need not be directly physically or electrically connected with another bioprinter capsule to transfer electric signals. For example, if bioprinter capsule 120A is connected to bioprinter capsule 120B, and bioprinter capsule 120B is connected to bioprinter capsule 120C, bioprinter capsule 120A can transfer power to bioprinter capsule 120C via bioprinter capsule 120B. In some embodiments, coupling component 128 may be further configured to provide structural support for an assembled bioprinter, ensuring the assembled bioprinter structure is stable and able to maintain its designed structure while carrying out bioprinting processes.

In some embodiments, interlocking surface 127 includes only coupling component 128, but in other embodiments interlocking surface includes both coupling component 128 and channel 129. Channel 129 is a tubular passage that connects to other channels on other bioprinter capsules. Channel 129 may be configured to transmit or receive a physical material between two bioprinter capsules, between two cartridge capsules, or between a bioprinter capsule and a cartridge capsule. Coupling component 128 surrounds channel 129 to ensure material transferred between channels of interconnected capsules is not lost or the flow of material disrupted. In other embodiments, coupling component can be separately located from channel 129 and channel 129 is configured to ensure there is not any material flow disruption or material loss. Some embodiments may be implemented, where interlocking surface 127 may include a plurality of channels 129 allowing different materials to flow through different channels 129. Channel 129 may be further configured to control the flow of material from bioprinter capsule 120 to bioprinter capsule 120A-120N and/or to cartridge capsule 130A-130N either by design or by instructions provided by bioprinting program 101.

In various embodiments of the present invention, cartridge capsules 130A-130N (hereinafter referred to generally as cartridge capsule 130 unless clarifying remarks are made when referring to more than one bioprinter capsule) include at least one cartridge magnetic signature 134A-134N, at least one cartridge camera 135A-135N, at least one cartridge sensor 136A-136N, and at least one interlocking surface 137A-137N (hereinafter referred to generally as cartridge magnetic signature, cartridge camera 135, cartridge sensor 136, and interlocking surface 137 respectively, unless clarifying remarks are made when referring to more than one cartridge capsule 130). Cartridge magnetic signature 134A-134N, cartridge camera 135A-135N, cartridge sensor 136A-136N, and interlocking surface 137A-137N are structurally and functionally similar to capsule magnetic signature 124A-124N, capsule camera 125A-125N, capsule sensor 126A-126N, and interlocking surface 127A-127 of bioprinter capsules 120A-120N.

In various embodiments, cartridge capsules 130A-130N are configured to house and provide biomaterial to bioprinter capsule 120 used to print various layers of a biostructure. For example, biomaterial is transferred from cartridge capsule 130 to bioprinter capsule 120 via channel 139. In an embodiment, cartridge capsule 130 programmatically controls the flow rate of biomaterial transferred from cartridge capsule 130 to bioprinter capsule 120. In an embodiment, the flow rate of biomaterial transferred from cartridge capsule 130 to bioprinter capsule 120 is programmatically controlled by bioprinting program 101. In an embodiment, biomaterial is passively transferred from cartridge capsule 130 to bioprinter capsule 120 based on pressure and diffusion of materials from high concentrations to low concentrations. In an embodiment, cartridge capsule 130 and/or bioprinter capsule 120 use microfluidic principles to release biomaterial at controlled intervals when introduced to a specific magnetic field. In an embodiment, bioprinter capsule 120 coupled to at least one cartridge capsule 130 may be configured such that biomaterial is deposited directly from the cartridge capsule 130 (without first being transferred to bioprinter capsule 120) to form one or more layers of a biostructure. In such an embodiment, bioprinter capsule 120 may be configured to control the movement as well as provide power to cartridge capsule 130 as instructed by bioprinting program 101.

Database 140 is a storage device capable of storing any type of data in a structured or an unstructured format. Database 140 includes bioprinter designs 142 and biostructure designs 146 that are accessible by bioprinting program 101 for assembling various assembled bioprinters and printing various biostructures, respectively. As used herein, a bioprinter design 142 may generally be understood as a file containing instructions on how to assemble a particular bioprinter having at least one bioprinter capsule 120A-120N and at least one cartridge capsule 130A-130N. Each bioprinter design 142 corresponds to readily available bioprinter capsules 120A-120N and cartridge capsules 130A-130N that can be connected to form an assembled bioprinter. Bioprinter design 142 further includes pre-considered bioprinter designs that include compatible combinations of bioprinter and cartridge capsule components. For example, bioprinter capsule 120A having a first magnetic signature may be connected to cartridge capsule 130A having a second, distinct magnetic signature since the first magnetic signature and the second magnetic signature are compatible with each other. In other words, when connected, the magnetic signatures of bioprinter capsule 120A and cartridge capsule 130A will not negatively interfere with the assembled bioprinter and movement of the assembled bioprinter during printing.

In some embodiments, a particular bioprinter design is chosen based, at least in part, on the complexity of the biostructure to be printed, as well as a patient's ability to swallow. Patients having difficulty swallowing capsules may be recommended a bioprinter design 142 having smaller ingestible bioprinter and cartridge capsules 120 and 130 or bioprinter assemblies that require fewer components.

In some embodiments, bioprinter designs 142 are retrieved from database 140 and loaded into memory of a bioprinter capsule 120. In other embodiments, bioprinter designs 142 are retrieved from database 140 and loaded into memory on computer system 110. In an embodiment, bioprinting program 101 selects one or more bioprinter designs 142 based on a patient diagnostic data report. For example, based on the diagnostic data report, bioprinting program 101 selects a particular bioprinter design based on identifying particular information in the diagnostic report associated with a damaged area of the digestive tract, such as the cause of the damage, and the physical structure of the damaged area, such as if the damaged area has irregular edges or protrusions. In an embodiment, a bioprinter design 142 is preselected by a user or system administrator (e.g., a medical professional or technician).

Biostructure designs 146 provide a plurality of printable biostructures that are intended to rectify an area of damaged digestive tract. Biostructure designs 146 include sets of instructions (similar to an STL file used in 3D printing) for printing each layer of a particular biostructure. Examples of instructional information included in a biostructure design include, but are not limited to: (i) what biomaterial should be used for printing a particular layer (e.g., hydrogels, mesh materials, synthetic materials intended to biomimic biological components, as well as various cell types (e.g., stem cells and/or donor cells); (ii) an internal location of a patient where the biomaterial should be printed or otherwise applied; (iii) x, y, and z coordinates for printing each layer; and (iv) a total number of layers of a biostructure. It should be appreciated that each biostructure design 146 may vary in complexity, ranging from complex vascular biostructures to simply printing or spraying one or more layers of biomaterial.

Figure 2:
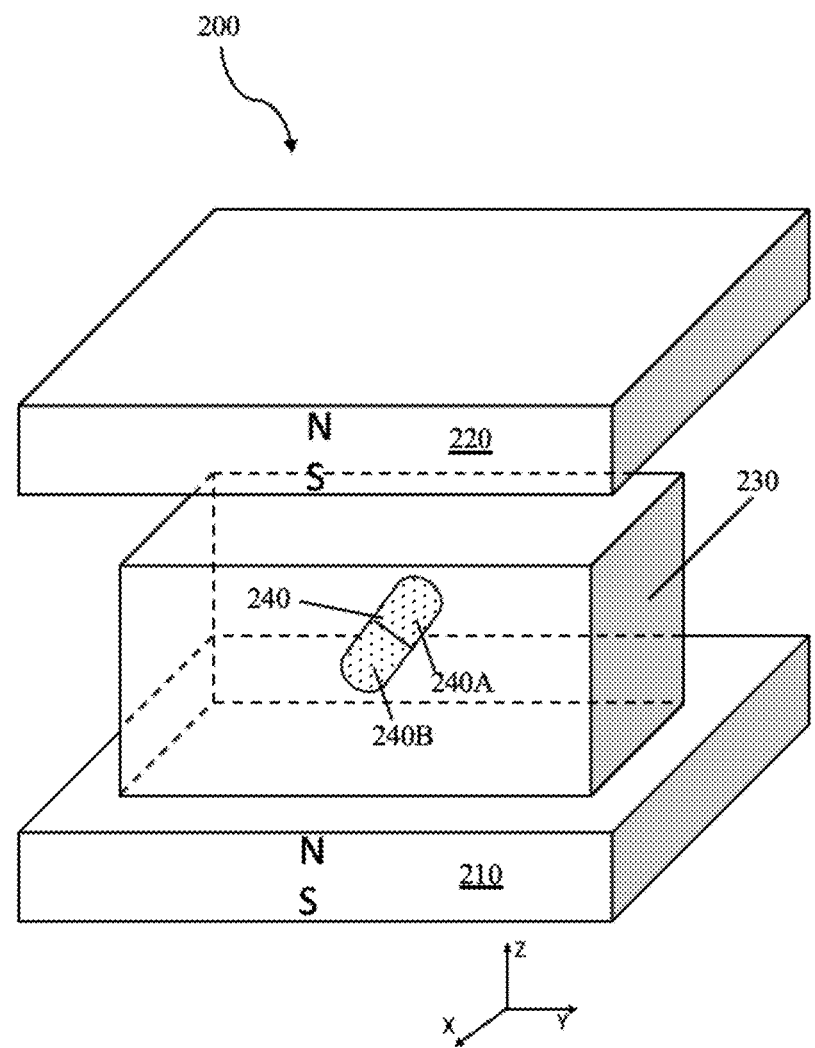
FIG. 2 illustrates an exemplary configuration of a magnetic field generator, generally designated 200, used to assemble bioprinter and cartridge capsules into an assembled bioprinter and perform bioprinting internally within the human body in accordance with at least one embodiment of the present invention.

FIG. 2 depicts an exemplary magnetic field generator, generally designated 200, used to assemble bioprinter and cartridge capsules into an assembled bioprinter and preform bioprinting internally within the human body in accordance with at least one embodiment of the present invention. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

As depicted in FIG. 2, magnetic field generator 200 includes bottom magnet 210, top magnet 220, container 230, and capsule 240. Bottom magnet 210 and top magnet 220 can include a single type of magnetic material or an array of magnetic materials capable of being programmatically controlled by bioprinting program 101. Container 230 is a simplified illustration representing an area of the patient's digestive tract, such as the stomach. While container 230 may be generally referred to herein as the stomach, container 230 may be representative of any area of the digestive tract or an internal area for which bioprinting is required. As depicted in FIG. 2, capsule 240 may be representative of a bioprinter capsule 120, a cartridge capsule 130, and/or a bioprinter assembly.

Bottom magnet 210 and top magnet 220 are configured to create a "push-pull" or "oppose-attract" effect on a magnetic signature of capsule 240. For example, bottom magnet 210 is configured to emit or produce a positive (i.e., North) magnetic field (indicated by the letter "N" and top magnet 220 is configured to produce a negative (i.e., South) magnetic field (indicated by the letter "S"). Accordingly, if a magnetic signature of capsule 240 has a predominately positive magnetic component, the positive magnetic field of bottom magnet 210 will oppose the predominately positive nature of the magnetic signature of capsule 240, thereby pushing capsule 240 in the opposite direction. When the opposing magnetic force produced by bottom magnet 210 is combined with the attractive force produced by top magnet 220 pulling capsule 240, capsule 240 is ultimately suspended within container 230. It should be appreciated that magnetic field generator 200 effectively reduces the effect of gravity on capsule 240 and allows capsule 240 to remain suspended and/or levitated within a predetermined range with respect to container 230. Here, the predetermined range is dictated by the particular magnetic field(s) acting on a particular magnetic signature of capsule 240.

In various embodiments, a magnetic signature of capsule 240 is configured to establish a particular, predetermined orientation internally within container 230 when subjected to one or more external magnetic fields generated by bottom magnet 210 and top magnet 220, respectively. In an embodiment, the magnetic signature is predesigned to orient capsule 240 at a particular position (e.g., 45 degrees), internally within a patient, based on the density distribution of capsule 240. In an embodiment, the magnetic signature of capsule 240 includes both a magnetic component, interacting directly with the external magnetic fields produced by bottom magnet 210 and top magnet 220, respectively, to suspend/levitate capsule 240 within a predetermined range within container 230, and a density distribution. For example, left side 240B may contain a material having a higher density than the material contained in right side 240A. As a result of the mass and density distribution between right side 240A and left side 240B, capsule 240 is oriented at 45 degrees when subjected to the external magnetic fields produced by bottom magnet 220 and top magnet 240.

In an embodiment, the magnetic signature of capsule 240 includes a magnetic distribution. The magnetic distribution utilizes either electromagnetic circuits or other magnetic materials to generate specific magnetic fields and magnetic properties across capsule 240 at predetermined areas. The magnetic fields and magnetic properties produced by the magnetic distribution interact with the magnetic fields produced by magnetic field generator 200 to cause capsule 240 to have a particular orientation while being suspended/levitated within a predetermined range of container 230. For example, the magnetic signature is predesigned to orient capsule 240 at a particular orientation (e.g., 45 degrees) internally within a patient, based on its magnetic distribution. In this example, a magnetic component or electromagnetic circuit is configured on left side 240B of capsule 240 to weakly oppose the magnetic field of bottom magnet 210 and a magnetic component or electromagnetic circuit on right side 240A of capsule 240 is configured to be strongly attracted to top magnet 220.

While only one capsule 240 is depicted in FIG. 2, it should be appreciated that bioprinter capsules 120A-120N and cartridge capsules 130A-130N may have unique magnetic signatures 134, respectively, that allow each capsule to be independently controlled by bioprinting program 101. Moreover, while bottom magnet 210 and top magnet 220, as depicted in FIG. 2, are described as having a positive magnetic field and a negative magnetic field that create a pushing/opposing force and a pulling/attracting force, respectively, on the magnetic signature of capsule 240, it should be appreciated that a negative magnetic field can be oriented to act as the pushing/opposing force while a negative magnetic field can be oriented to act as a pulling/attracting force.

Figure 3:
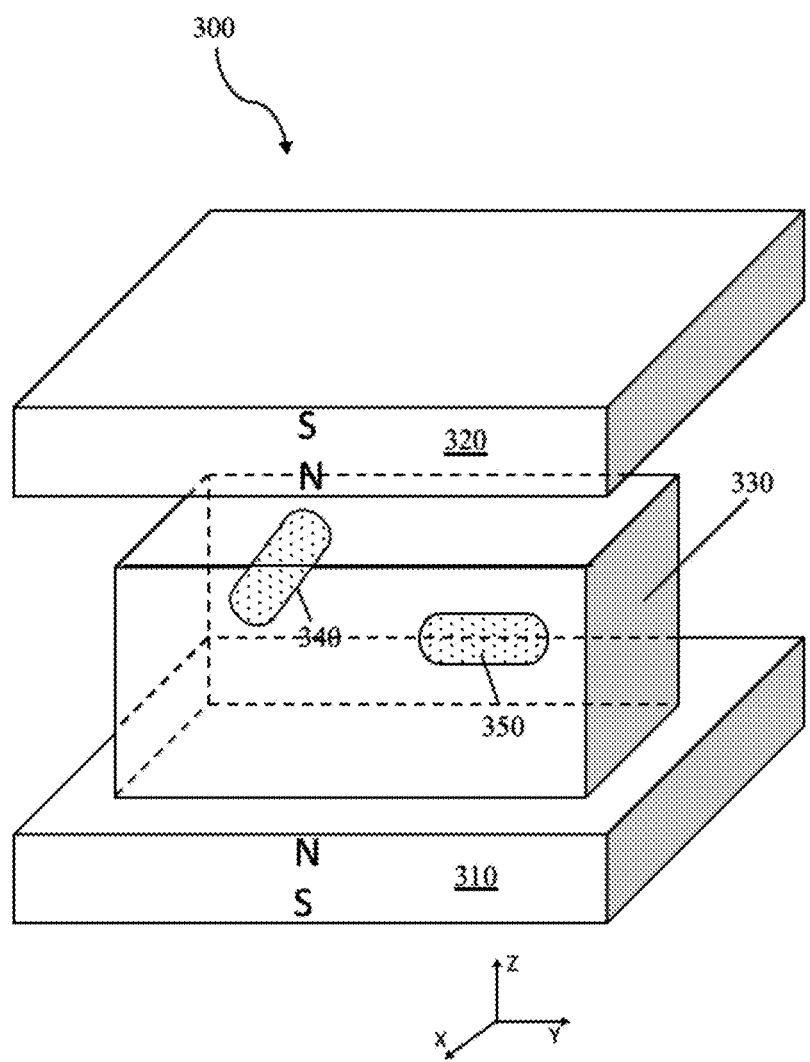
FIG. 3 illustrates an exemplary configuration of magnetic field generator, generally designated 300, used to assemble bioprinter and cartridge capsules into an assembled bioprinter and perform bioprinting internally within the human body in accordance with at least one embodiment of the present invention.

FIG. 3 depicts an exemplary magnetic field generator, generally designated 300, suitable for orienting two capsules internally within the human body in accordance with at least one embodiment of the present invention. FIG. 3 provides only an illustration of one implementation and does not imply any limitations with regard to the environments in which different embodiments may be implemented. Many modifications to the depicted environment may be made by those skilled in the art without departing from the scope of the invention as recited by the claims.

As depicted in FIG. 3, magnetic field generator 300 includes bottom magnet 310, top magnet 320, container 330, first capsule 340, and second capsule 350. Bottom magnet 310 and top magnet 320 may include a single magnetic type or an array of magnetic types (e.g., one or more permanent magnets, one or more electromagnetics, or any combination thereof) capable of being programmatically controlled by bioprinting program 101. Container 330 is a simplified illustration representing an area of the patient's digestive tract, such as a stomach. While container 330 may be generally referred to herein as the stomach, container may be representative of any area of the digestive tract or an internal area for which bioprinting is required. First capsule 340 and second capsule 350 may be representative of a bioprinter capsule 120, a cartridge capsule 130, a bioprinter assembly, and or any possible combination thereof.

As depicted in FIG. 3, the stomach or container 330 is flooded with paramagnetic material. In an embodiment, container 330 is flooded for the duration of the assembly and/or the printing process. In an embodiment, container 330 is only flooded for either the bioprinter assembly or the bioprinting process. It should be appreciated that by flooding container 330 with paramagnetic material, capsule 340 and 350 need not have magnetic signatures formed from complex electromagnetic circuits or magnetic components particularly distributed throughout capsules 340 and 350. However, it should be noted that electromagnetic circuits and/or magnetic components may be used to form respective magnetic signatures of capsule 340 and capsule 350 when flooding container 330 with paramagnetic material. It should further be appreciated that although not discussed herein, container 330 may instead be flooded with diamagnetic material. Similarly, capsule 340 and capsule 350 may instead have magnetic signatures formed based, at least in part, by paramagnetic material.

One of ordinary skill in the art will appreciate that paramagnetic materials have unpaired electrons that are attracted by an externally applied magnetic field and can be found in gaseous or liquid solutions. When an external magnetic field is applied, a magnetic field is induced in the paramagnetic materials in the same direction of the applied external magnetic field. Available paramagnetic materials may include any known gaseous and/or liquid solution that is considered non-toxic and biocompatible. It should be appreciated that in addition to increasing the strength of a magnetic field, the use of a liquid paramagnetic material also allows for the use of heavier capsules when implementing general density principles coupled with the particular configurations of the magnetic signatures of the capsules. Similarly, the use of a liquid paramagnetic material also allows for the use of magnets or magnetic materials having weaker magnetic fields used to carry out assembly and bioprinting in accordance with various embodiments of the present invention.

As further depicted in FIG. 3, bottom magnet 310, oriented below container 330 and top magnet 320, oriented above container 330, are configured to emit or produce a positive magnetic field, respectively, that is directed towards container 330 (positive magnetic fields are indicated by the letter "N" and negative magnetic fields are indicated by the letter "S"). While FIG. 3 depicts bottom magnet 310 and top magnet 320 as positive magnetic fields, bottom and top magnets 310 and 320 simply need to be directing like poles, with opposing magnetic fields directed towards container 330. Accordingly, in other embodiments, bottom magnet 310 and top magnet 320 may each be configured to direct negative magnetic fields towards container 330. Each of bottom magnet 310 and top magnet 320 may be configured by bioprinting program 101 to respectively direct one or more magnetic fields having varying magnetic field strengths towards container 330.

In some embodiments, capsules 340 and 350 have magnetic signatures that include one or more of, but not limited to, capsule shape, capsule density distribution, a particular arrangement of magnetic components (e.g., any type of magnetic material, such as diamagnetic material), and electromagnetic circuits. Capsule 340 and capsule 350 may include the same magnetic signatures or separate, distinct magnetic signatures. As depicted in FIG. 3, capsule 340 and capsule 350 have different orientations and positions within container 330 due to capsule 340 and capsule 350 having different magnetic signatures. In an embodiment, capsule 340 and capsule 350 are positioned and/or oriented within container 330 based on a respective density component associated with their magnetic signatures. In an embodiment, capsule 340 and capsule 350 are positioned and/or oriented container 330 based on a respective shape associated with their magnetic signatures. For example, a capsule having a triangular shape may orient itself within the paramagnetic material differently than the same capsule having an oval shape.

In an embodiment, capsule 340 and 350 are positioned and/or oriented within container 330 based on respective diamagnetic materials associated with their magnetic signatures. When an external magnetic field is directed towards a diamagnetic material, a magnetic field is induced in the opposite direction to the external magnetic field direction. When two like and opposing poles, depicted as bottom magnet 310 and top magnet 320, are directed towards capsule 340 or 350 having a diamagnetic material as part of its magnetic signature, the orientation and/or location of capsule 340 or 350 can be predetermined based the magnetic field strength of bottom magnet 310 and top magnet 320. In an embodiment, bottom magnet 310 and top magnet 320 are permanent magnets. Here, the position and/or orientation of capsule 340 and 350 having respective diamagnetic materials can be altered by altering a position of bottom magnet 310 and top magnet 320 with respect to capsule 340 and capsule 350. In an embodiment, bottom magnet 310 and top magnet 320 are electromagnets. Here, the position and/or orientation of capsule 340 and capsule 350 having respective diamagnetic materials can be altered by altering (increasing or decreasing) an electric current of bottom magnet 310 and top magnet 320 with respect to capsule 340 and capsule 350 to alter the magnetic field generated by bottom magnet and top magnet 320.

Figure 4:
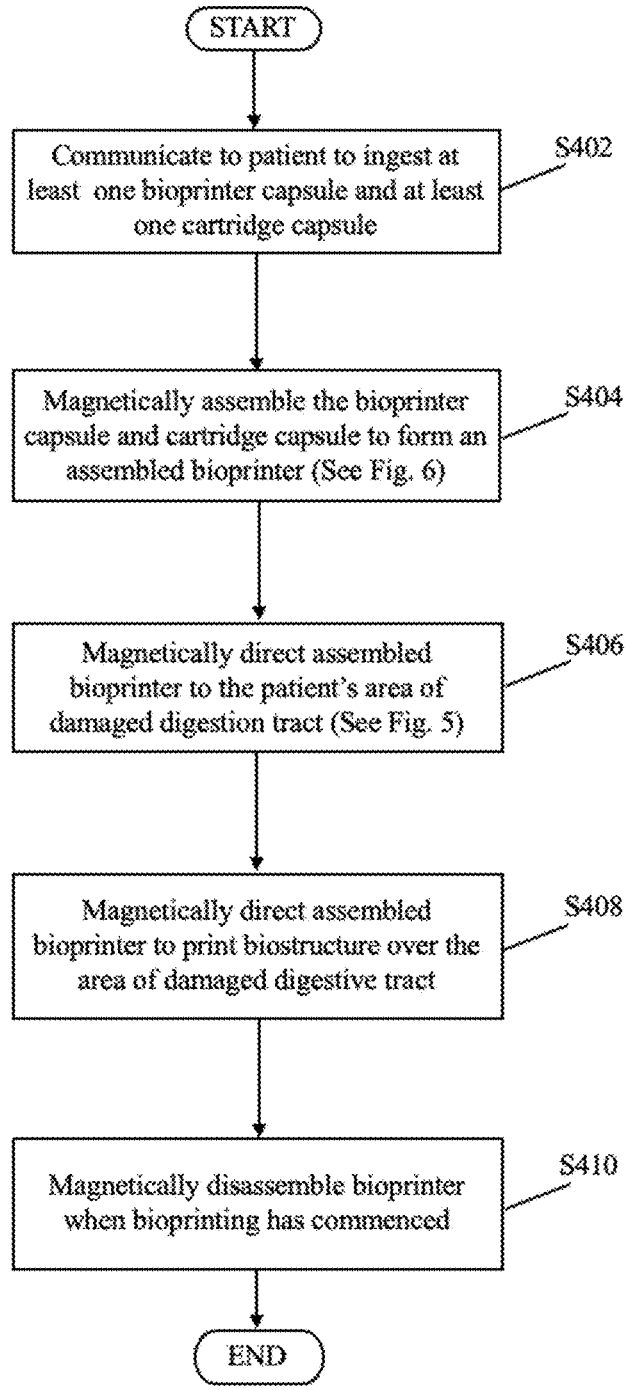
FIG. 4 is a flow chart diagram depicting operational steps by bioprinting program 101 for assembling an assembled bioprinter and performing bioprinting internally within the human body in accordance with at least one embodiment of the present invention.

FIG. 4 is a flow chart diagram depicting operational steps for by bioprinting program 101 for assembling an assembled bioprinter and performing bioprinting internally within the human body in accordance with at least one embodiment of the present invention. FIG. 4 provides only an illustration of one implementation and does not imply any limitations with regard to the environments in which different embodiments may be implemented. Many modifications to the depicted environment may be made by those skilled in the art without departing from the scope of the invention as recited by the claims. Additionally, elements and identifiers discussed in reference to FIG. 1, FIG. 2, and FIG. 3, may be carried over to FIG. 4 only to denote similar structures and provide clarity. The use of identifiers used in these previous figures should not be construed as limiting substitutions in reference to other embodiments discussed in reference to any other figure.

At step S402, bioprinting program 101 instructs a patient to ingest one or more bioprinter capsules 120A-120N and one or more cartridge capsules 130A-130N. The number and type of bioprinter capsules 120A-120N and cartridge capsules 130A-130N are selected in accordance with a predetermined bioprinter design 142 for printing a particular 3D biostructure. In some embodiments, bioprinting program 101 instructs the patient to ingest specific bioprinter capsules 120A-120N and cartridge capsules 130A-130N at specific time intervals. This allows for a bioprinter to be assembled one capsule at a time and can be used to reduce interference between different magnetic signatures of bioprinter capsules 120A-120N and cartridge capsules 130A-130N when connecting respective bioprinter capsules 120A-120N and cartridge capsules 130A-130N with one another. For example, a bioprinter design 142 requires the use of four capsules: bioprinter capsule 120A, bioprinter capsule 120B, bioprinter cartridge 120C, and cartridge capsule 130A. Continuing with this example, bioprinter capsules 120A and 120B have already been ingested and connected together via their respective interlocking surfaces to form a partially assembled bioprinter. Bioprinter capsule 120C is subsequently ingested and connected to bioprinter capsules 120A and 120B prior to ingesting cartridge capsule 130A. Accordingly, the potential for any interferences posed by the external magnetic fields acting on the magnetic signatures of respective bioprinter and/or cartridge capsules when assembly the bioprinter capsules and/or cartridge capsules is mitigated. However, in some embodiments, bioprinter capsules 120A-120N and cartridge capsules 130A-130N may be ingested in any order. For example, the respective magnetic signatures of bioprinter capsules 120A-120N and cartridge capsules 130A-130N are predesigned to be compatible with one another, and therefore, will not interfere in such way that could reduce the effectiveness of magnetically assembling the bioprinter or the bioprinting process.

At Step S404, bioprinting program 101 magnetically assembles the one or more bioprinter capsules 120A-120N and the one or more cartridge capsule 130A-130N to form an assembled bioprinter. Bioprinting program 101 configures magnetic field generator 102 to produce particular magnetic fields that are directed towards a bioprinter capsule and/or cartridge capsule and allows for the capsules to be suspended/levitated or be suspended/levitated internally within the patient at a predetermined range. As discussed in detail above, each of bioprinter capsule and cartridge capsule has a magnetic signature that interacts with the magnetic fields produced by magnetic field generator 102 to reduce the effects of gravity, thereby enabling the capsules to be suspended or levitated. While Step S404 is discussed generally with reference to FIG. 4, Step 406 will be further discussed in greater detail below with reference to FIG. 5.

At Step S406, bioprinting program 101 magnetically directs the assembled bioprinter to the patient's damaged are of the digestive tract. In some embodiments, at least one of the capsules of the assembled bioprinter, either bioprinter capsule 120 or cartridge capsule 130, includes a capsule camera 125. Capsule camera 125 is capable of capturing image data and transmitting the image data to bioprinting program 101. In some embodiments, bioprinting program 101 analyzes the image data to direct the assembled bioprinter to the damaged area of the patient's digestive tract. In some embodiments, bioprinting program 101 receives location data with respect to the location of the damaged area from a system administrator (e.g., medical staff or technicians). While Step S406 is discussed generally with reference to FIG. 4, Step S406 will be further discussed in greater detail below with reference to FIG. 5.

At Step S408, bioprinting program 101 magnetically directs the assembled bioprinter to print a biostructure over the area of damaged digestive tissue. The printing process, controlled by bioprinting program 101, can range in complexity from spraying layers of cells onto an area of damaged digestive tract to printing complex digestive tissue. In an exemplary embodiment, bioprinting program 101 controls the printing process of an assembled bioprinter formed from a first bioprinter capsule 120A that houses a scrubber/finisher, a capsule camera 125A interconnected to bioprinter capsule 120A, a first cartridge capsule 130A, a second cartridge capsule 130B, and other bioprinter components (not depicted) that may be required for bioprinting. In this exemplary embodiment, if the damaged area of digestive tissue has irregular edges that could inhibit and/or reduce the efficacy of printing the rectifying biostructure, bioprinting program 101 can direct and instruct the assembled bioprinter to remove irregular edges or debris to the damaged area using the scrubber/finisher functional unit on the assembled bioprinter. It should be noted that in some instances the damaged area need not be scrubbed prior to printing a first layer onto the damaged area.

Bioprinting program 101 moves the assembled bioprinter to print a first layer of biomaterial, as determined by the biostructure design 146, housed in a cartridge capsule. Bioprinting program 101 configures magnetic field generator 102 and the associated one or more magnetic fields generated to induce the assembled bioprinter to move in the 3D coordinate planes (e.g., the xy-plane) as determined by biostructure design 146. Bioprinting program 101 alters the magnetic fields to ensure that the assembled bioprinter is moved to print biomaterial at a specific coordinate(s). In order for the assembled bioprinter to move to the next coordinate increment, bioprinting program 101 again alters the one or more magnetic fields to move the assembled bioprinter to that coordinate location. Bioprinting program 101 receives coordinate instructions from biostructure design 146 designating how each layer should be printed. Bioprinting program 101 uses this information to determine a sequential series of steps wherein at each step the one or more magnetic field is alter in such a way as to move the assembled bioprinter from one increment to the next. For example, bioprinting program 101 alters the one or more external magnetic fields in a series of sequential steps to move the assembled bioprinter incrementally throughout the xy-plane (i.e., the plane comprising the biostructure layer to be printed).

In some embodiments, the first layer includes a mesh material that provides support for additional layers, as well as support to the various substructures of the biostructure. Mesh materials may include biocompatible materials including, but not limited to, hydrogels, glycogen, and other biomolecules or synthetic components configured to support the printable biostructure. In some embodiments, bioprinting program 101 receives image data from capsule camera 125 during printing of the first layer. In an embodiment, based on the image data captured during printing, bioprinting program 101 can determine when printing of the first layer is complete. In an embodiment, the first layer is determined to be complete based on completing the first layer of a biostructure design 146. If bioprinting program 101 determines that the first layer is incomplete, bioprinting program 101 continues to direct the assembled bioprinter during printing of the first layer. Printing subsequent layers are accomplished similar to printing of the first layer. However, if a different material is required to print a subsequent layer, bioprinting program 101 can stop the flow of biomaterial from one cartridge capsule and start the flow of a second, distinct biomaterial from another cartridge capsule. For example, a first cartridge capsule may include specific cell types necessary to print a tissue layer and a second cartridge capsule may include medications that can be sprayed onto the damaged area to aid in the healing of the damaged area. While Step S408 is discussed generally with reference to FIG. 4, Step S408 will be further discussed in greater detail with reference to FIG. 5.

At Step S410, after the bioprinting is complete, bioprinting program 101 disassembles the assembled bioprinter into individual components.

Figure 5:
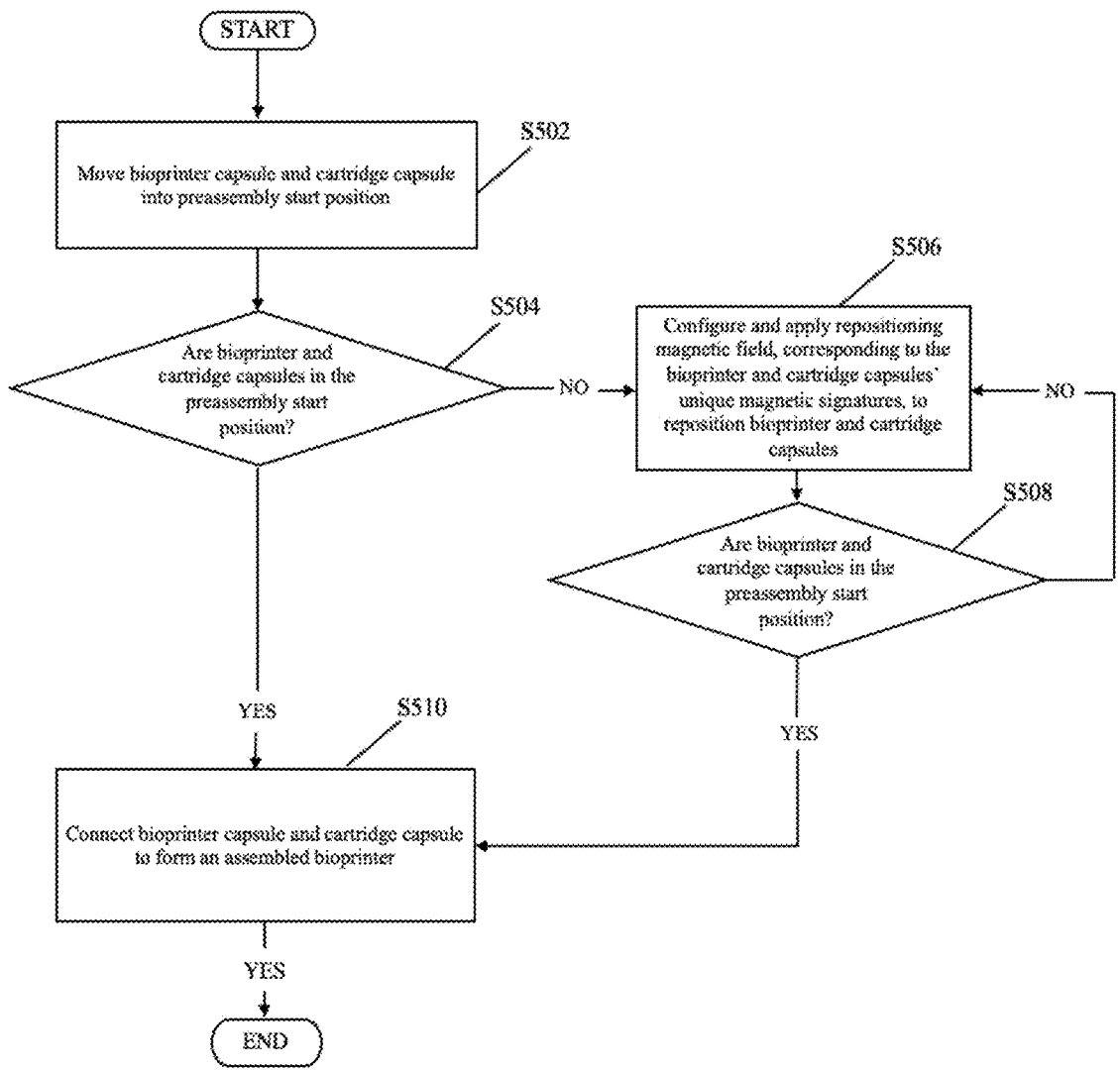
FIG. 5 is a flow chart diagram depicting operational steps by bioprinting program 101 for assembling an assembled bioprinter in accordance with at least one embodiment of the present invention.

FIG. 5 is a flow chart diagram depicting operational steps for connecting bioprinter capsule 120 and cartridge capsule 130 to form an assembled bioprinter in accordance with at least one embodiment of the invention. FIG. 5 provides only an illustration of one implementation and does not imply any limitations with regard to the environments in which different embodiments may be implemented. Many modifications to the depicted environment may be made by those skilled in the art without departing from the scope of the invention as recited by the claims. While FIG. 5 refers generally to components discussed in FIGS. 2 and 3, any magnetic configuration discussed in reference to magnetic field generator 102 may be used. Additionally, elements and identifiers discussed in reference to FIG. 1, FIG. 2, and FIG. 3, may be carried over to FIG. 5 only to denote similar structures and provide clarity. The use of identifiers used in these previous figures should not be construed as limiting substitutions in reference to other embodiments discussed in reference to any other figure.

At Step S502, bioprinting program 101 directs one or more external magnetic fields towards bioprinter capsule 120 and cartridge capsule 130 internally located within a patient to cause bioprinter capsule 120 and cartridge capsule 130 to obtain a preassembled start position. Preassembled start position may generally be understood as a particular location and/or orientation of one or more bioprinter capsules 120A-120N, one or more cartridge capsules 130A-130N, and or any possible combination thereof required for connecting respective bioprinter capsules 120A-120N and respective cartridge capsules 130A-130 in a particular arrangement. Bioprinter capsule 120 and cartridge capsule 130 are moved into the preassembled start position based, at least in part, an interaction of the one or more external magnetic fields with a particular magnetic signature of each of bioprinter capsule 120 and cartridge capsule 130. It should be appreciated that each magnetic signature of a capsule should automatically orient and position bioprinter capsule 120 and/or cartridge capsule 130 when introduced into one or more particular magnetic fields. However, for a variety of reasons (e.g., the strength or direction of a magnetic field), instances may occur where bioprinter capsule 120 and/or cartridge capsule 130 do not automatically position and/orient themselves into the preassembled start position.

At decision Step S504, bioprinting program 101 determines whether bioprinter capsule 120 and cartridge capsule 130 are in the preassembly start position. Here, bioprinting program 101 compares the position and orientation of bioprinter capsule and cartridge capsule 130, respectively to predetermined locations and orientations corresponding to the preassembly start position. If bioprinting program 101 determines that bioprinter capsule 120 and cartridge capsule 130 are in the preassembly start position (decision step "YES" branch), bioprinting program 101 proceeds to step S510, and bioprinter capsule 120 and cartridge capsule 130 are connected to form an assembled bioprinter. If bioprinting program 101 determines that bioprinter capsule 120 and cartridge capsule 130 are not in the preassembly start position (decision step "NO" branch), bioprinting program 101 proceeds to Step S506.

At step S506, bioprinting program 101 alters one or more external magnetic fields directed towards bioprinter capsule 120 and/or cartridge capsule 130 to reposition and/or orient a misaligned capsule into the preassembly start position. It should be appreciated that bioprinting program 101 may alter one or more external magnetic fields in any particular manner as discussed herein to move bioprinter capsule 120 and/or cartridge capsule 130. For example, bioprinting program 101 may reposition bioprinter capsule 120 and or cartridge capsule 130 in a manner substantially similar to moving an assembled bioprinter into an initial printing position discussed in step S602 of FIG. 6 below.

At decision step S508, bioprinting program 101 determines whether bioprinter capsule 120 and cartridge capsule 130 are in the preassembly start position after altering the one or more external magnetic fields in accordance with step S506. Here, bioprinting program 101 compares the position and orientation of bioprinter capsule and cartridge capsule 130 (after step S506) to predetermined locations and orientations corresponding to the preassembly start position. If bioprinting program 101 determines that bioprinter capsule 120 and cartridge capsule 130 are not in the preassembly start position (decision step "NO" branch), bioprinting program 101 returns to step S506. If bioprinting program 101 determines that bioprinter capsule 120 and cartridge capsule 130 are in the preassembly start position, bioprinting program 101 proceeds to Step S510.

At step S510, bioprinting program 101 connects bioprinter capsule 120 and cartridge capsule 130 to form an assembled bioprinter. Bioprinter capsule 120 and cartridge capsule 130 are connected at their respective interlocking surfaces, interlocking surface 127 and interlocking 137. Here, bioprinting program 101 configures interlocking surface 127 and interlocking surface 137 to connect. Interlocking surface 127 and interlocking surface 137 can be configured in any particular manner discussed herein.

Figure 6:
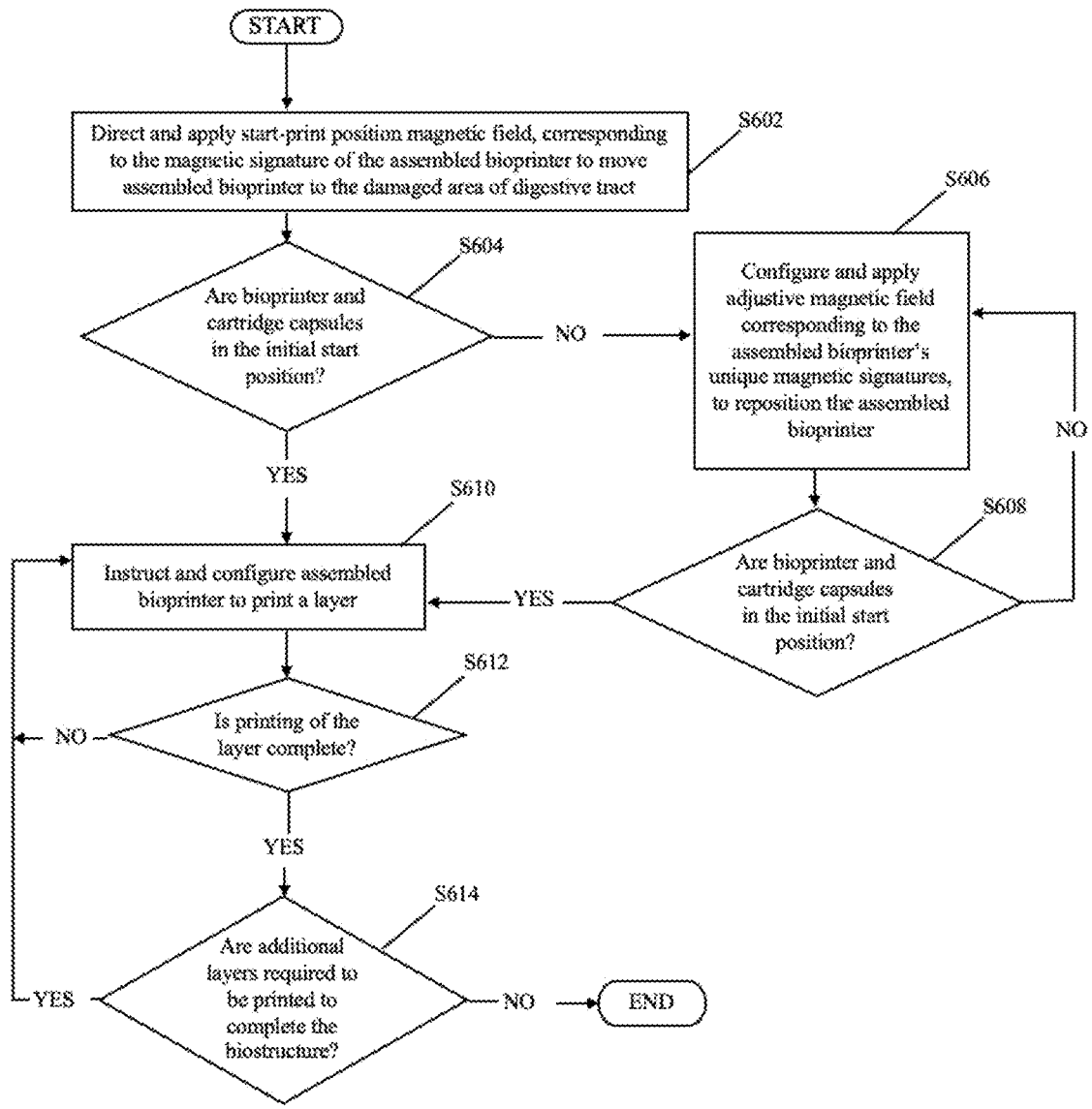
FIG. 6 is a flow chart diagram depicting operational steps by bioprinting program 101 for performing bioprinting in accordance with at least one embodiment of the present invention.

FIG. 6 is a flow chart diagram depicting operational steps by bioprinting program 101 for performing bioprinting using the bioprinter assembled in FIG. 5 in accordance with at least one embodiment of the present invention. FIG. 6 provides only an illustration of one implementation and does not imply any limitations with regard to the environments in which different embodiments may be implemented. Many modifications to the depicted environment may be made by those skilled in the art without departing from the scope of the invention as recited by the claims. Additionally, elements and identifiers discussed in reference to FIG. 1, FIG. 2, and FIG. 3, may be carried over to FIG. 6 only to denote similar structures and provide clarity. The use of identifiers used in these previous figures should not be construed as limiting substitutions in reference to other embodiments discussed in reference to any other figure.

At Step S602, bioprinting program 101 directs one or more external magnetic fields towards the assembled bioprinter internally located within the patient to cause the assembled bioprinter to obtain an initial printing position. An initial printing position may generally be understood as a particular location and/or orientation required by the assembled bioprinter to begin printing a first layer of a biostructure onto the damaged area. In an embodiment, the assembled bioprinter is moved into the initial printing position based on introducing one or more additional external magnetic fields that interact with the magnetic signatures of respective capsules that form the assembled bioprinter to cause the assembled bioprinter to obtain the initial printing position. In an embodiment, the assembled bioprinter is moved into the initial printing position based on altering one or more external magnetic fields directed towards the assembled bioprinter. In an embodiment, the assembled bioprinter is moved into the initial printing position based on introducing one or more additional external magnetic fields and already one or more pre-existing magnetic fields. It should be appreciated that based on the particular magnetic signatures of the capsules that form the assembled bioprinter, the assembled bioprinter should automatically orient itself into the initial print position when subject to the additional and/or altered external magnetic fields. However, for a variety of reasons (e.g., the strength or direction of magnetic field), instances may occur where the assembled bioprinter does not automatically position and/or orient itself into the initial print position.

At decision Step S604, bioprinting program 101 determines whether the assembled bioprinter is in the initial printing position. Here, bioprinting program 101 compares the location and orientation information of the assembled bioprinter to a predetermined location and orientation corresponding to the initial printing position (e.g., the initial printing position may be designated in a biostructure design for printing a particular biostructure. If bioprinting program 101 determines that the assembled bioprinter is in the initial print position (decision step "YES" branch), bioprinting program 101 proceeds to step S610. If bioprinting program 101 determines that the assembled bioprinter is not in the initial print position (decision Step "NO" branch), bioprinting program 101 proceeds to step S606.

At step S606, bioprinting program 101 alters one or more external magnetic fields directed towards the assembled bioprinter to reposition and/or orient the assembled bioprinter into the initial printing position. It should be appreciated that bioprinting program 101 may alter one or more external magnetic fields in any particular manner as discussed herein to move the assembled bioprinter. For example, bioprinting program 101 may reposition the assembled bioprinter in a manner substantially similar to moving the assembled bioprinter into the initial printing position discussed in step S602 of FIG. 6 above.

At decision step S608, bioprinting program 101 determines whether the assembled bioprinter is in the initial printing position after altering the one or more external magnetic fields in accordance with step S606. Here, bioprinting program 101 compares the position and orientation of the assembled bioprinter (after step S606) to the predetermined location and orientation corresponding to the initial printing position. If bioprinting program 101 determines that the assembled bioprinter is not in the initial printing position (decision step "NO" branch), bioprinting program 101 returns to step S606. If bioprinting program 101 determines that the assembled bioprinter is in the initial printing position (decision step "YES" branch, bioprinting program 101 proceeds to Step S610.

At Step S610, bioprinting program 101 moves the assembled bioprinter to print a layer of a biostructure onto the internally damaged area of the patient. In various embodiments, bioprinting moves the assembled bioprinter to print a particular layer of a biostructure based, at least in part, on sequentially altering one or more external magnetic fields directed towards the assembled bioprinter. The sequential alteration of the one or more external magnetic fields corresponds to an incremental movement of the assembled bioprinter along at least one plane. In an embodiment, sequentially altering one or more magnet fields includes inversely increasing and decreasing a magnetic field strength a first electromagnet and a second electromagnet, respectively. For example, a pair of electromagnets may be arranged along the x-axis with respect to the assembled bioprinter such that sequentially inversely increasing the magnetic field strength of one magnet and decreasing the magnetic field strength of the other magnet in the pair causes the assembled bioprinter to incrementally move in a direction along the x-axis. By controlling the current applied, bioprinting program 101 can produce subtle changes in the magnetic field where the opposing magnetic field strength of the left electromagnet of the horizontal pair is increased and the attractive magnetic field of the right electromagnet is decreased. The change in the magnetic field induces the assembled bioprinter to move towards the right. By inversely altering the magnetic field strength of the horizontal pair, the assembled bioprinter can move in the x and y directions (i.e., back and forth between the right and left electromagnet). Similarly, a pair of electromagnets may be arranged along the y-axis with respect to the assembled bioprinter such that sequentially inversely increasing the magnetic field strength of one magnet and decreasing the magnetic field strength of the other magnet in the pair causes the assembled bioprinter to incrementally move in a direction along the y-axis. Likewise, a pair of electromagnets may be arranged along the z-axis with respect to the assembled bioprinter such that sequentially inversely increasing the magnetic field strength of one magnet and decreasing the magnetic field strength of the other magnet in the pair causes the assembled bioprinter to incrementally move in a direction along the z-axis. Thus, when working in concert, as directed by bioprinting program 101, the horizontal pair control movement of the assembled bioprinter within each layer while the vertical pair controls the suspension and height of the bioprinter ensuring that as each layer is printed, that the assembled bioprinter is suspended at the correct height necessary to properly print various layers of the biostructure.

It should be noted that this process may similarly be performed for printing additional layers of a biostructure. In other words, a first layer may be formed by incrementally moving the assembled bioprinter in a direction along the x-plane, a second layer formed by incrementally moving the assembled bioprinter in a direction along the y-plane, a third layer formed by incrementally moving the assembled bioprinter in a direction along the x-plane, etc. It should be further noted that as each additional layer is printed, bioprinting program 101 incrementally moves the assembled bioprinter in a direction along the z-plane, as each additional layer increases the height of the overall printed biostructure in the z-axis.

In an embodiment, a single cartridge capsule includes a sufficient amount of biomaterial required to print a complete biostructure. In an embodiment, a plurality of cartridge capsules are required to print the biostructure. In some embodiments, bioprinting program 101 determines when a cartridge capsule has been emptied of biomaterial. In these embodiments, bioprinting program 101 will instruct and direct assembled bioprinter to print from an additional, already attached cartridge capsule, or a secondary cartridge capsule can be used. In embodiments using a second cartridge capsule, bioprinting program 101 halts the bioprinting process and controls and configures magnetic field generator 102 and the capsule magnetic signatures 134 of the assembled bioprinter to remove the empty cartridge capsule and assemble the second cartridge capsule to reform the assembled bioprinter. In this example, after the bioprinter has been reformed with the secondary cartridge capsule, bioprinting program 101 instructs the assembled bioprinter to restart the printing process at the precise moment the printing process was previously interrupted.

At decision Step S612, bioprinting program 101 determines whether the current printed layer is completed. Here, bioprinting program 101 compares the biostructure design 146 and the layer instructions to the layer that has been printed. If bioprinting program 101 determines that the current printed layer is complete (decision step "YES" branch), bioprinting program 101 proceeds to decision step S614. If bioprinting program 101 determines that the current printed layer is not complete (decision step "NO" branch), bioprinting program 101 returns to Step S610.

At decision Step S614, bioprinting program 101 determines whether an additional layer is required for printing the biostructure. In some embodiments, bioprinting program 101 compares the biostructure design 146 to the layer(s) that have been completed to determine if the printing of the biostructure is complete. In some embodiments bioprinting program 101 determines if the biostructure is completed using image data received from a capsule camera. In an embodiment, although printing of the biostructure may be complete, bioprinting program determines (e.g., via image data received from a capsule camera) that the biostructure and/or the surrounding area contains irregular surfaces and/or debris that could affect the efficacy of the printed biostructure. Here, bioprinting program 101 may instruct a scrubber/finisher functional unit of the assembled bioprinter to remove the irregular surfaces and/or debris.

If bioprinting program 101 determines that there is an additional layer(s) that requiring printing (decision step "YES" branch), bioprinting program 101 returns to step S610. If bioprinting program 101 determines there are no additional layers that require printing, (decision step "NO" branch), the process ends.

Figure 7:
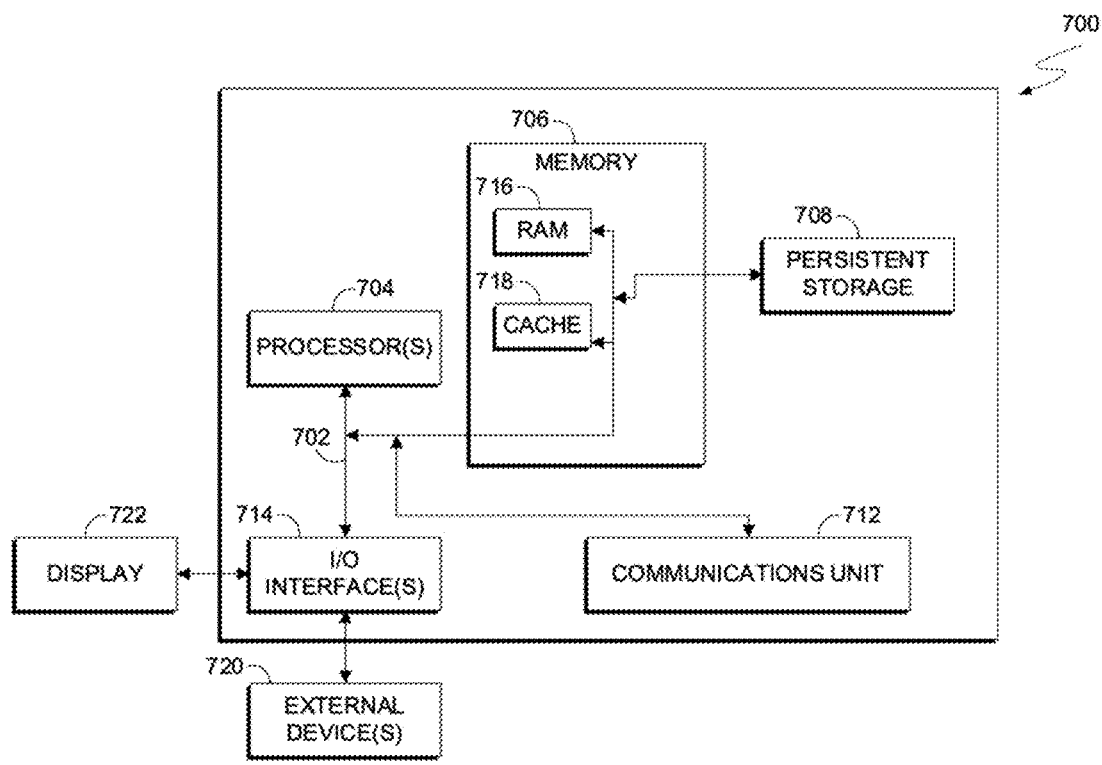
FIG. 7 is a block diagram depicting components of a computing device, generally designated 700, suitable for executing bioprinting program 101 in accordance with at least one embodiment of the present invention.

FIG. 7 is a block diagram depicting components of a computing device, generally designated 700, suitable for bioprinting program 101 in accordance with at least one embodiment of the invention. Computing device 700 includes one or more processor(s) 704 (including one or more computer processors), communications fabric 702, memory 706 including, RAM 716 and cache 718, persistent storage 708, communications unit 712, I/O interface(s) 714, display 722, and external device(s) 720. It should be appreciated that FIG. 7 provides only an illustration of one embodiment and does not imply any limitations with regard to the environments in which different embodiments may be implemented. Many modifications to the depicted environment may be made.

As depicted, computing device 700 operates over communications fabric 702, which provides communications between computer processor(s) 704, memory 706, persistent storage 708, communications unit 712, and input/output (I/O) interface(s) 714. Communications fabric 702 can be implemented with any architecture suitable for passing data or control information between processor(s) 704 (e.g., microprocessors, communications processors, and network processors), memory 706, external device(s) 720, and any other hardware components within a system. For example, communications fabric 702 can be implemented with one or more buses.

Memory 706 and persistent storage 708 are computer readable storage media. In the depicted embodiment, memory 706 includes random-access memory (RAM) 716 and cache 718. In general, memory 706 can include any suitable volatile or non-volatile one or more computer readable storage media.

Program instructions for bioprinting program 101 can be stored in persistent storage 708, or more generally, any computer readable storage media, for execution by one or more of the respective computer processor(s) 704 via one or more memories of memory 706. Persistent storage 708 can be a magnetic hard disk drive, a solid-state disk drive, a semiconductor storage device, read-only memory (ROM), electronically erasable programmable read-only memory (EEPROM), flash memory, or any other computer readable storage media that is capable of storing program instructions or digital information.

Media used by persistent storage 708 may also be removable. For example, a removable hard drive may be used for persistent storage 708. Other examples include optical and magnetic disks, thumb drives, and smart cards that are inserted into a drive for transfer onto another computer readable storage medium that is also part of persistent storage 708.

Communications unit 712, in these examples, provides for communications with other data processing systems or devices. In these examples, communications unit 712 can include one or more network interface cards. Communications unit 712 may provide communications through the use of either or both physical and wireless communications links. In the context of some embodiments of the present invention, the source of the various input data may be physically remote to computing device 700 such that the input data may be received, and the output similarly transmitted via communications unit 712.

I/O interface(s) 714 allows for input and output of data with other devices that may operate in conjunction with computing device 700. For example, I/O interface(s) 714 may provide a connection to external device(s) 720, which may be as a keyboard, keypad, a touch screen, or other suitable input devices. External device(s) 720 can also include portable computer readable storage media, for example thumb drives, portable optical or magnetic disks, and memory cards. Software and data used to practice embodiments of the present invention can be stored on such portable computer readable storage media and may be loaded onto persistent storage 708 via I/O interface(s) 714. I/O interface(s) 714 also can similarly connect to display 722. Display 722 provides a mechanism to display data to a user and may be, for example, a computer monitor.

What is claimed is:

1. A computer-implemented method of 3D printing a biostructure on an internally damaged area of a patient, comprising:
   assembling a first bioprinter capsule and a first cartridge capsule to form an assembled bioprinter internally within the patient based, at least in part, on directing one or more external magnetic fields towards a first bioprinter capsule and a first cartridge capsule, wherein:
       the first bioprinter capsule includes a first magnetic signature and at least one interlocking surface; and
       the first cartridge capsule includes a second magnetic signature and at least one interlocking surface;
   moving the assembled bioprinter to the internally damaged area of the patient based, at least in part, on altering the one or more external magnetic fields directed towards the assembled bioprinter; and
   printing, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

2. The computer-implemented method of claim 1, wherein each of the first magnetic signature and the second magnetic signature are formed based, at least in part, from one or more magnetic materials, wherein the one or more magnetic materials includes electromagnets, permanent magnets, paramagnetic materials, and diamagnetic materials.

3. The computer-implemented method of claim 1, wherein each of the first magnetic signature and the second magnetic signature are further formed based, at least in part, from one or more of a magnetic distribution, a density distribution, and a shape distribution.

4. The computer-implemented method of claim 1, wherein the one or more external magnetic fields, directed towards the first bioprinter capsule and the first cartridge capsule, are configured to magnetically interact with the first and second magnetic signatures, to control the position and orientation of the first bioprinter capsule and the first cartridge capsule.

5. The computer-implemented method of claim 1, wherein the at least one interlocking surface of the first bioprinter capsule and the at least one interlocking surface of the first cartridge capsule are further configured to lock together.

6. The computer-implemented method of claim 1, wherein both the at least one interlocking surface of the first bioprinter capsule and the at least one interlocking surface of the first cartridge capsule include a coupling component.

7. The computer-implemented method of claim 6, wherein the coupling component is configured to transfer power between the first bioprinter capsule and the first cartridge capsule.

8. The computer-implemented method of claim 6, wherein the coupling component further includes electronic locking circuitry configured to electrically lock the coupling component of the first bioprinter capsule to the coupling component of the first cartridge capsule.

9. The computer-implemented method of claim 1, wherein the at least one interlocking surface of the first bioprinter capsule and the at least one interlocking surface of the first cartridge capsule further include a channel, wherein the channel of the first bioprinter capsule and the first cartridge capsule are aligned.

10. The computer-implemented method of claim 9, wherein the channel is further configured to provide a first biomaterial housed within the first cartridge capsule to the first bioprinter cartridge capsule.

11. The computer-implemented method of claim 10, wherein the channel is further configured to control the flow and movement of the first biomaterial between the first bioprinter capsule and the first cartridge capsule.

12. The computer-implemented method of claim 1, wherein the one or more external magnetic fields are produced by a magnetic field generator.

13. The computer-implemented method of claim 11, wherein the magnetic field generator includes at least one magnetic material selected from the group consisting of electromagnets, permanent magnets, and temporary magnets, therein the at least one magnetic material generates one or more magnetic fields.

14. The computer-implemented method of claim 1, wherein the assembled bioprinter prints a mesh layer on the internally damaged area of the patient.

15. The computer-implemented method of claim 1, wherein the first biostructure is selected from a biostructure design database comprised of printing instructions for the assembled bioprinter and the one or more external magnetic fields.

16. The computer-implemented method of claim 1, wherein a secondary assembled bioprinter is assembled inside the patient to work together with the assembled bioprinter to print the first biostructure.

17. The computer-implemented method of claim 1, wherein the assembled bioprinter is selected from a bioprinter design database comprised of assembly instructions for the one or more external magnetic fields.

18. The computer-implemented method of claim 1, wherein the first bioprinter capsule further includes a capsule camera, configured to capture image data of the patient.

19. A computer program product for 3D printing a biostructure on an internally damaged area of a patient, the computer program product comprising one or more computer readable storage media and program instructions stored on the one or more computer readable storage media, the program instructions including instructions to:
assemble a first bioprinter capsule and a first cartridge capsule to form an assembled bioprinter internally within the patient based, at least in part, on directing one or more external magnetic fields towards a first bioprinter capsule and a first cartridge capsule, wherein:
the first bioprinter capsule includes a first magnetic signature and at least one interlocking surface; and
the first cartridge capsule includes a second magnetic signature and at least one interlocking surface;
move the assembled bioprinter to the internally damaged area of the patient based, at least in part, on altering the one or more external magnetic fields directed towards the assembled bioprinter; and
print, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

20. A computer system for 3D printing a biostructure on an internally damaged area of a patient, the computer system comprising:
one or more computer processors;
one or more computer readable storage media;
computer program instructions;
the computer program instructions being stored on the one or more computer readable storage media for execution by the one or more computer processors; and
the computer program instructions including instructions to:
assemble a first bioprinter capsule and a first cartridge capsule to form an assembled bioprinter internally within the patient based, at least in part, on directing one or more external magnetic fields towards a first bioprinter capsule and a first cartridge capsule, wherein:
the first bioprinter capsule includes a first magnetic signature and at least one interlocking surface; and
the first cartridge capsule includes a second magnetic signature and at least one interlocking surface;

move the assembled bioprinter to the internally damaged area of the patient based, at least in part, on altering the one or more external magnetic fields directed towards the assembled bioprinter; and print, via the assembled bioprinter, a first biostructure onto the internally damaged area of the patient based, at least in part, on altering the one or more external magnetic fields directed towards the assembled bioprinter, wherein the one or more external magnetic fields are sequentially altered to incrementally move the assembled bioprinter along at least one plane.

\* \* \* \* \*